United States Patent
Hwang et al.

(10) Patent No.: US 9,775,828 B2
(45) Date of Patent: Oct. 3, 2017

(54) PHARMACEUTICAL COMPOSITION WITH INCREASED SOLUBILITY BY USING SACCHARIN

(71) Applicant: University-Industry Foundation, Yonsei University, Seoul (KR)

(72) Inventors: Sung-Joo Hwang, Seoul (KR); Han Kang, Incheon (KR); In-ho Song, Gyeonggi-do (KR); Sang Min Hyun, Jeju-do (KR); Min Jun Kwon, Busan (KR); Taek Sun Kim, Daegu (KR); Sitaram Prasad Velaga, Luleå (SE)

(73) Assignee: University-Industry Foundation, Yonsei University, Seoul (KR)

( * ) Notice: Subject to any disclaimer, the term of this patent is extended or adjusted under 35 U.S.C. 154(b) by 0 days.

(21) Appl. No.: 14/926,078

(22) Filed: Oct. 29, 2015

(65) Prior Publication Data

US 2016/0120983 A1 May 5, 2016

(30) Foreign Application Priority Data

Oct. 29, 2014 (KR) ........................ 10-2014-0148179

(51) Int. Cl.

| A61K 31/404 | (2006.01) |
|---|---|
| A61K 31/422 | (2006.01) |
| A61K 47/26 | (2006.01) |
| A61K 9/08 | (2006.01) |
| A61K 31/4045 | (2006.01) |

(52) U.S. Cl.
CPC .............. *A61K 31/404* (2013.01); *A61K 9/08* (2013.01); *A61K 31/4045* (2013.01); *A61K 31/422* (2013.01); *A61K 47/26* (2013.01)

(58) Field of Classification Search
CPC ..... A61K 31/404; A61K 31/422; A61K 47/22
See application file for complete search history.

(56) References Cited

U.S. PATENT DOCUMENTS

| 2007/0166336 A1 | 7/2007 | Delmarre et al. |
| 2012/0046244 A1* | 2/2012 | Rogers ............... A61K 47/4803 514/75 |

FOREIGN PATENT DOCUMENTS

| KR | 10-0670092 | 1/2007 |
| WO | WO 01/39772 | 6/2001 |

OTHER PUBLICATIONS

Office Action dated Feb. 1, 2016 from the Korean Patent Office Re. Application No. 10-2014-0148179.
Carter et al. "Sweet Success: Ionic Liquids Derived from Non-Nutritive Sweeteners", Chemistry Communications, 6(2004): 630-631.

* cited by examiner

Primary Examiner — James D Anderson

(57) ABSTRACT

The present invention provides a pharmaceutical composition including an ionic liquid composed of a triptan compound and saccharin. Since a triptan compound and saccharin form an ionic liquid to increase the solubility of the triptan compound in the present invention, it is possible to expect a rapid and high dissolution of the triptan compound when a pharmaceutical composition is prepared. In addition, large amounts of organic solvents and acidic solvents need not be used in order to dissolve the triptan compound.

9 Claims, 2 Drawing Sheets

PHARMACEUTICAL COMPOSITION WITH INCREASED SOLUBILITY BY USING SACCHARIN

RELATED APPLICATION

This application claims the benefit of priority of Korean Patent Application No. 10-2014-0148179 filed on Oct. 29, 2014, the contents of which are incorporated herein by reference in their entirety.

FIELD AND BACKGROUND OF THE INVENTION

The present invention relates to a pharmaceutical composition which has the increased solubility of a triptan compound by using saccharin.

A triptan compound is an agonist selective for serotonin, acts on $5\text{-HT}_{1B1D}$ to constrict expanded blood vessels, and may be used for migraines with aura or sudden severe migraines without aura.

In general, the triptan compound is orally administered and taken, and usually administered in the form of a tablet or a capsule, and in recent years, development has been conducted to administer the triptan compound as an orally disintegration tablet (ODT), an orally disintegration film (ODF) or a nasal formulation capable of being easily administered to patients, children, or the aged, which have difficulty in swallowing the tablet or the capsule, without water.

Zolmitriptan is a triptan-based compound (hereinafter, referred to as a triptan compound), the chemical name thereof is (S)-4-{{3-[2-(dimethylaminoethyl)]-1H-indol-5-1}methyl}-2-oxazolidinone, the solubility thereof to water is 1.3 mg/ml (25° C.), and the bioavailability thereof is about 40% when administered to the oral cavity and the nasal cavity.

Zolmitriptan is a tablet and may be administered in an amount of up to 10 mg a day, and a tablet (Zomig, AstraZeneca, United Kingdom) and an orally disintegration tablet (Zomig ZMT, AstraZeneca, United Kingdom) have been developed in 2 mg and 5 mg dosage forms.

Saccharin is a generally recognized as safe (GRAS) material, and is known to be 500 times or more sweeter than sugar. Saccharin is variously used as a food additive or a pharmaceutical additive. Further, saccharin acts as a co-former in the co-crystal technology, and has been reported to be capable of increasing the solubility of a drug due to the interaction with indomethacin and carbamazepine.

Patent Document 1 describes that zolmitriptan was dissolved in an acidic medium to prepare zolmitriptan into a dosage form suitable for nasal administration in the form of a salt, but there was inconvenience in that a phosphate should be further added thereto in order to adjust the acidic zolmitriptan salt to a desired pH.

CITATION LIST

Patent Document (Patent Document 1) 1. Korean Publication No. 2002-0058051.

SUMMARY OF THE INVENTION

The present invention has been made in an effort to prepare a new pharmaceutical composition which improves properties of a triptan compound by using saccharin.

An exemplary embodiment of the present invention provides a pharmaceutical composition including an ionic liquid composed of a triptan compound and saccharin.

Another exemplary embodiment of the present invention provides a method for preparing a pharmaceutical composition, the method including: preparing an ionic liquid by mixing a triptan compound and saccharin.

Yet another exemplary embodiment of the present invention provides a pharmaceutical composition for preventing or treating migraines, sudden severe migraines, or cluster migraines, the pharmaceutical composition including: an ionic liquid composed of a triptan compound and saccharin.

Since a triptan compound and saccharin form an ionic liquid to increase the solubility of the triptan compound in the present invention, it is possible to expect a rapid and high dissolution of the triptan compound when a pharmaceutical composition is prepared. In addition, large amounts of organic solvents and acidic solvents need not be used in order to dissolve the triptan compound.

DETAILED DESCRIPTION

Figure 1:
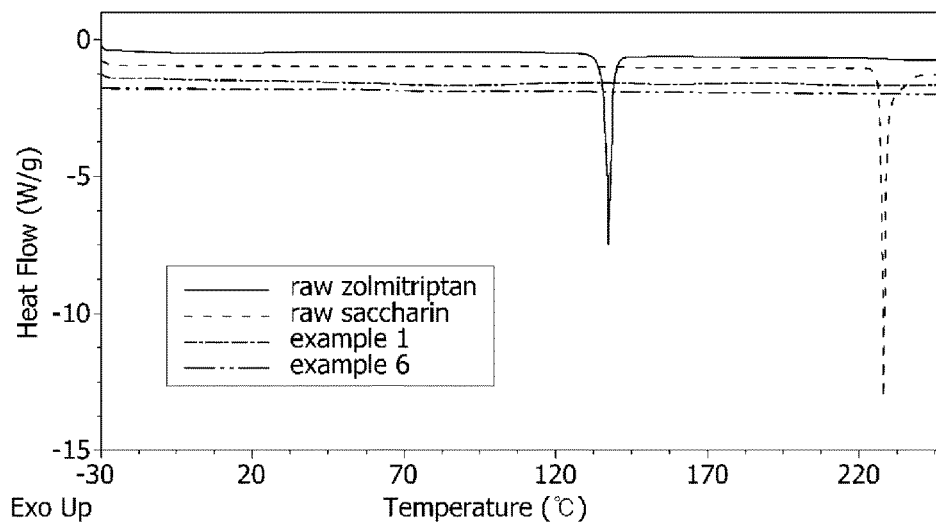
FIG. 1 illustrates the DSC analysis results of pharmaceutical compositions prepared according to the Examples of the present invention.

The present invention relates to a pharmaceutical composition including an ionic liquid composed of a triptan compound and saccharin.

Hereinafter, a pharmaceutical composition according to the present invention will be described in more detail.

The pharmaceutical composition according to the present invention includes an ionic liquid composed of a triptan compound and saccharin.

The triptan compound is an agonist selective for serotonin, and may be used as an agonist for $5\text{-HT}_{1B1D}$.

This kind of triptan compound is not particularly limited, and it is possible to use one or more selected from the group consisting of zolmitriptan, sumatriptan, rizatriptan, almotriptan, naratriptan, eletriptan, avitriptan, and frovatriptan.

The triptan compound may be included in an amount of 30 to 90 parts by weight, 30 to 70 parts by weight, or 30 to 65 parts by weight, based on 100 parts by weight of a pharmaceutical composition. Within the range, the triptan compound may have excellent solubility to water, and may be present as an ionic liquid.

In the present invention, saccharin may be used in order to improve properties of the triptan compound. Specifically, the solubility of the triptan compound may be increased, and the triptan compound may be present as an ionic liquid by lowering the melting point, by using saccharin.

The saccharin was added in a small amount to food additives or pharmaceuticals and used as a sweetener to block the taste in the related art, but may be used as a solubilizer to improve the solubility of the triptan compound in the present invention.

The saccharin may be included in an amount of 10 to 70 parts by weight, 30 to 70 parts by weight, or 45 to 70 parts by weight, based on 100 parts by weight of a pharmaceutical composition. Within the range, saccharin and the triptan compound may form an ionic liquid to enhance the solubility.

The weight ratio of the triptan compound and saccharin may be 30:70 to 90:10, 30:70 to 70:30, or 30:70 to 65:45.

Further, the molar ratio of the triptan compound and saccharin may be 1:5 to 5:1, 1:3 to 3:1, or 1:1.

The above-described triptan compound and saccharin are present as an ionic liquid.

In the present invention, the ionic liquid means an ionic compound which is composed of positive ions and negative ions and is a liquid at normal temperature. That is, the ionic liquid may be composed only of positive ions and negative ions like salts while being a liquid.

The ionic liquid may also be used as a meaning that includes not only a liquid state having fluidity, but also a paste state having viscosity.

The ionic liquid according to the present invention may be present as an ionic liquid at −30 to 250° C., specifically, a normal temperature of 15 to 25° C. In general, zolmitriptan among triptan compounds has a melting point of 132 to 137° C. and saccharin has a melting point of 225 to 230° C., so that the triptan compound and saccharin are present as a solid at normal temperature. However, in the present invention, the triptan compound may be present as an ionic liquid in a liquid state by saccharin rather than a solid. Specifically, the triptan compound and saccharin may be present as a positive ion and a negative ion, respectively, in the ionic liquid.

In the present invention, the pharmaceutical composition has excellent solubility in water by including the ionic liquid, and a separate acidic solvent need not be used in order to dissolve the triptan compound when the pharmaceutical compound is sprayed into the nasal cavity or oral cavity. Further, even when the pharmaceutical composition is used as an orally disintegration tablet and an orally disintegration film, an organic solvent need not be used, and the amount of an excipient may also be reduced due to the reduction in amount of the organic solvent used.

In the present invention, the pharmaceutical composition is used for preventing or treating migraines, sudden severe migraines, or cluster migraines.

In addition, the present invention relates to a method for preparing the above-described pharmaceutical composition.

The pharmaceutical composition according to the present invention may be prepared by a step of preparing an ionic liquid by mixing a triptan compound and saccharin.

The kind and content of the triptan compound and saccharin may be the above-described kind and content.

In an exemplary embodiment, the ionic liquid may be prepared by mixing a triptan compound and saccharin, and then milling the mixture. Through the milling, the triptan compound and saccharin may be obtained as a mixture in a liquid state, that is, an ionic liquid. The milling may be performed for 10 to 100 minutes or 20 to 60 minutes. In the present invention, a reaction may be performed by adding 500 µl or less, 400 µl or less, or 300 µl or less of water in order to shorten the time for preparing the ionic liquid. In this case, the reaction may be performed for 5 to 10 minutes.

Furthermore, in an exemplary embodiment, an ionic liquid may be prepared by separately dissolving a triptan compound and saccharin in a solvent, and then mixing the dissolved triptan compound and saccharin, and performing a solvent evaporation method. Further, the ionic liquid may be prepared by dissolving the triptan compound and saccharin together in the solvent, and then performing a solvent evaporation method.

The solvent evaporation method may be performed in the atmospheric state, but may be performed under reduced pressure and dry conditions. Through the solvent evaporation method, an ionic liquid is precipitated.

In this case, the solvent may be selected from the group consisting of ethanol and methanol, and specifically, ethanol may be used.

Further, the present invention relates to a method for preventing or treating migraines, sudden severe migraines, or cluster migraines, comprising administering an effective amount of the pharmaceutical composition.

In the method, the pharmaceutical composition including: an ionic liquid composed of a triptan compound and saccharin.

The pharmaceutical composition according to the present invention may have a form suitable for oral administration, topical administration, inhalation administration, insufflation administration or parenteral administration.

The pharmaceutical composition of the present invention may include one or more pharmaceutically acceptable carriers in addition to the ionic liquid which is an active ingredient. The term 'pharmaceutically acceptable carrier' means a publicly known pharmaceutical excipient which is useful when a pharmaceutically active compound for administration is formulated and is in fact non-toxic and insensitive under the conditions of use. The exact ratio of the excipient is determined by the solubility and chemical characteristics of the active compound, the selected administration route, and the standard pharmaceutical practice.

The pharmaceutical composition of the present invention may be formulated into a form suitable for a desired administration method by using an adjuvant, such as an excipient, a disintegrant, a sweetener, a binder, a coating agent, a swelling agent, a lubricant, a glidant, a flavor, and an antioxidant, which is suitable and physiologically acceptable.

The pharmaceutical composition may be formulated in the form of a tablet, a capsule, a pill, a granule, a powder, an injection, a liquid, or a film, but the form thereof is not limited thereto.

The dosage form of the pharmaceutical composition and the pharmaceutically acceptable carrier may be appropriately selected according to the technology publicly known in the art, and for example, the following documents may be referred to: [Urquhart et al., Lancet, 16:367, 1980]; [Lieberman et al., PHARMACEUTICAL DOSAGE FORMS-DISPERSE SYSTEMS, 2nd ed., vol. 3, 1998]; [Ansel et al., PHARMACEUTICAL DOSAGE FORMS & DRUG DELIVERY SYSTEMS, 7th ed., 2000]; [Martindale, THE EXTRA PHARMACOPEIA, 31st ed.]; [Remington's PHARMACEUTICAL SCIENCES, 16th-20th editions]; [THE PHARMACOLOGICAL BASIS OF THERAPEUTICS, Goodman and Gilman, eds., 9th ed., 1996]; [Wilson and Gisvolds' TEXTBOOK OF ORGANIC MEDICINAL AND PHARMACEUTICAL CHEMISTRY, Delgado and Remers, eds., 10th ed., 1998]. Further, it is also possible to refer to, for example, the following documents [Platt, Clin. Lab. Med., 7:289-99, 1987]; [Aulton, PHARMACEUTICS: THE SCIENCE OF DOSAGE FORM DESIGN, Churchill Livingstone, N.Y., 1988]; [EXTEMPORANEOUS ORAL LIQUID DOSAGE PREPARATIONS, CSHP, 1998], ["DRUG DOSAGE," J. Kans. Med. Soc., 70(1):30-32, 1969], and the like for the principle of formulating the pharmaceutical composition.

In one exemplary embodiment, the pharmaceutical composition may be for use in combination with a second drug.

In the present invention, the term 'second drug' means a pharmaceutically active ingredient other than the triptan compound of the present invention. The triptan compound of the present invention may be used for treating migraines, sudden severe migraines, or cluster migraines as described above. Accordingly, the triptan compound of the present invention may be used in combination with a second drug for efficiently treating the diseases.

When the triptan compound according to the present invention and the second drug may be administered by the same method, the triptan compound may also be provided in the form of a complex formulation which is formulated with the second drug.

Meanwhile, in the present invention, the term 'subject' means a warm-blooded animal such as a mammal with a specific condition, disorder or disease, and includes, for example, a human, an orangutan, a chimpanzee, a mouse, a rat, a dog, a cow, a chicken, a pig, a goat, a sheep, and the like, but the subject is not limited thereto.

In addition, the term 'treating' includes relieving a symptom, temporarily or permanently eliminating causes of the symptom, or preventing or hindering occurrence of the symptom or progression of the aforementioned condition, disorder or disease, but the treating is not limited thereto.

An effective amount of the active ingredient of the pharmaceutical composition according to the present invention means an amount required to treat a disease. Therefore, the effective amount of the active ingredient may be adjusted according to various factors such as the kind and severity of disease, the kinds and contents of active ingredient and other ingredients contained in the composition, the kind of dosage form, age, body weight, general medical conditions, gender and diet of a patient, duration and route of administration, a secretion rate of the composition, treatment duration, and the number of drugs used together.

Zolmitriptan may be administered to a patient, such that, for example, a unit dose of 0.5 to 15 mg (for example, 1.0 mg, 2.5 mg, 5.0 mg, and 10 mg) is delivered to the patient. Such a unit dosage may be administered at any step in the initial or middle stage of the onset of migraines, and typically administered once or three times a day.

EXAMPLES

Hereinafter, the present invention will be described in more detail through the Examples which follow the present invention and the Comparative Examples which do not follow the present invention, but the scope of the present invention is not limited by the Examples suggested below.

Examples 1 to 5

A composition was prepared by placing zolmitriptan (Sinoway Industrial, China) and saccharin (Acros, USA), which are present in the contents in the following Table 1, in a mortar, and grinding and mixing the ingredients with a pestle for 30 minutes.

TABLE 1

| | Zolmitriptan (mg) | Saccharin (mg) | Weight ratio of zolmitriptan:saccharin | Molar ratio |
|---|---|---|---|---|
| Example 1 | 574 | 366 | 61:39 | 1:1 |
| Example 2 | 574 | 732 | 44:56 | 1:2 |
| Example 3 | 574 | 1098 | 34:66 | 1:3 |
| Example 4 | 574 | 183 | 76:24 | 2:1 |
| Example 5 | 574 | 122 | 82:18 | 3:1 |

Examples 6 to 10

Zolmitriptan and saccharin present in the contents in the following Table 2 were placed in an Erlenmeyer flask and ethanol was added thereto to dissolve zolmitriptan and saccharin in a sonicator for 15 minutes.

The ethanol solution, in which zolmitriptan and saccharin were dissolved, was transferred to a round bottom flask, and the flask was mounted on a reduced pressure drying apparatus to remove all the ethanol for about 2 hours, thereby obtaining a mixture of zolmitriptan and saccharin (pharmaceutical composition) precipitated on the wall surface of the round bottom flask.

TABLE 2

| | Zolmitriptan (mg) | Saccharin (mg) | Ethanol (ml) | Weight ratio of zolmitriptan:saccharin | Molar ratio |
|---|---|---|---|---|---|
| Example 6 | 574 | 366 | 50 | 61:39 | 1:1 |
| Example 7 | 574 | 732 | 50 | 44:56 | 1:2 |
| Example 8 | 574 | 1098 | 50 | 34:66 | 1:3 |
| Example 9 | 574 | 183 | 50 | 76:24 | 2:1 |
| Example 10 | 574 | 122 | 50 | 82:18 | 3:1 |

Examples 11

A composition was prepared by placing sumatriptan and saccharin (Acros, USA), which are present in the contents in the following Table 3, in a mortar, and grinding and mixing the ingredients with a pestle for 30 minutes.

Examples 12

Sumatriptan and saccharin present in the contents in the following Table 3 were placed in an Erlenmeyer flask and ethanol was added thereto to dissolve sumatriptan and saccharin in a sonicator for 15 minutes.

The ethanol solution, in which sumatriptan and saccharin were dissolved, was transferred to a round bottom flask, and the flask was mounted on a reduced pressure drying apparatus to remove all the ethanol for about 2 hours, thereby obtaining a mixture of sumatriptan and saccharin (pharmaceutical composition) precipitated on the wall surface of the round bottom flask.

in the following Tables 4 and 5. In Tables 4 and 5, the number in the parenthesis denotes the weight of zolmitriptan contained in the pharmaceutical composition.

Next, the solubility was measured by allowing the pharmaceutical composition to stand under the conditions of 37±0.5° C. at 100 rpm in a lateral direction in a water bath, taking only the supernatant, and using HPLC.

TABLE 4

| Classification | Zolmitriptan | Example 1 | Example 2 | Example 3 | Example 4 | Example 5 |
|---|---|---|---|---|---|---|
| Weight (mg) | 200 | 327 (200) | 455 (200) | 582 (200) | 263 (200) | 242 (200) |

TABLE 5

| Classification | Zolmitriptan | Example 6 | Example 7 | Example 8 | Example 9 | Example 10 |
|---|---|---|---|---|---|---|
| Weight (mg) | 200 | 327 (200) | 455 (200) | 582 (200) | 263 (200) | 242 (200) |

TABLE 3

| | Sumatriptan (mg) | Saccharin (mg) | Ethanol (ml) | Weight ratio of Suamatriptan:saccharin | Molar ratio |
|---|---|---|---|---|---|
| Example 11 | 590 | 366 | 0 | 62:38 | 1:1 |
| Example 12 | 590 | 366 | 50 | 62:38 | 1:1 |

Experimental Example 1. Measurement of State of Pharmaceutical Composition

The pharmaceutical compositions prepared in Examples 1 and 6 among examples 1 to 10 were subjected to thermal analysis by using the differential scanning calorimetry (DSC). The state was measured in a temperature range of −30 to 250° C., and the warming rate was 10° C./min.

The measurement result is illustrated in FIG. 1.

As a result of the measurement, it can be confirmed that the melting point of zolmitriptan is 132° C. to 137° C., the melting point of saccharin is 225 to 230° C., and those ingredients are present as a solid at normal temperature, but the mixture of zolmitriptan and saccharin in Examples 1 and 6 is present in a liquid or glassy state in the measurement range.

Figure 2:
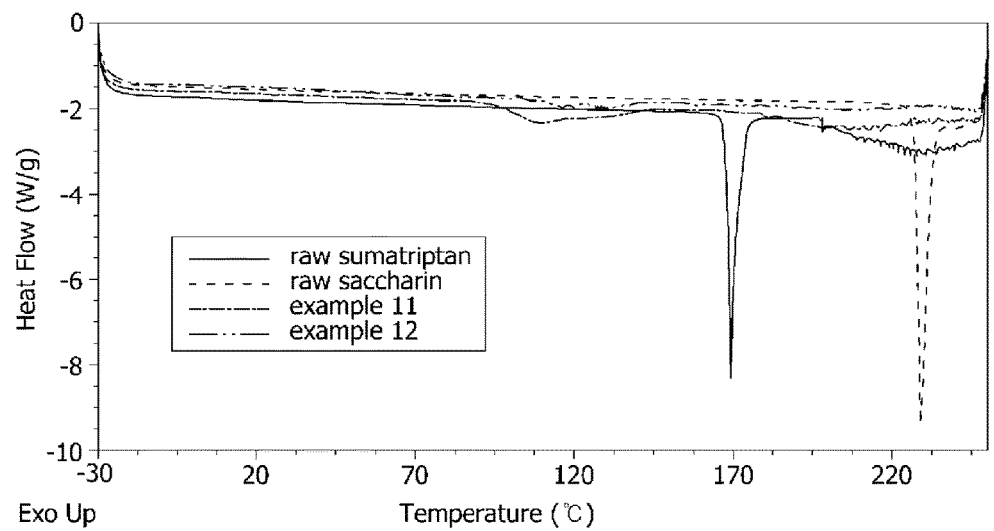
FIG. 2 illustrates the DSC analysis results of pharmaceutical compositions prepared according to the Examples 11 and 12 of the present invention.

In addition, the measurement result of Examples 11 and 12 is illustrated in FIG. 2.

As a result of the measurement, the mixture of sumatriptan and saccharin is present in a liquid or glassy state in the measurement range.

Experimental Example 2. Solubility Experiment

The solubilities of the pharmaceutical compositions prepared in Examples 1 to 10 and zolmitriptan in water were compared.

The pharmaceutical compositions prepared in Examples 1 to 10 and zolmitriptan were placed in 20 ml vials, 10 ml of distilled water was added thereto, and the vials were hermetically sealed with lids. In this case, the contents of the pharmaceutical compositions and zolmitriptan are shown as The HPLC measurement results are illustrated in FIG. 3.

Figure 3:
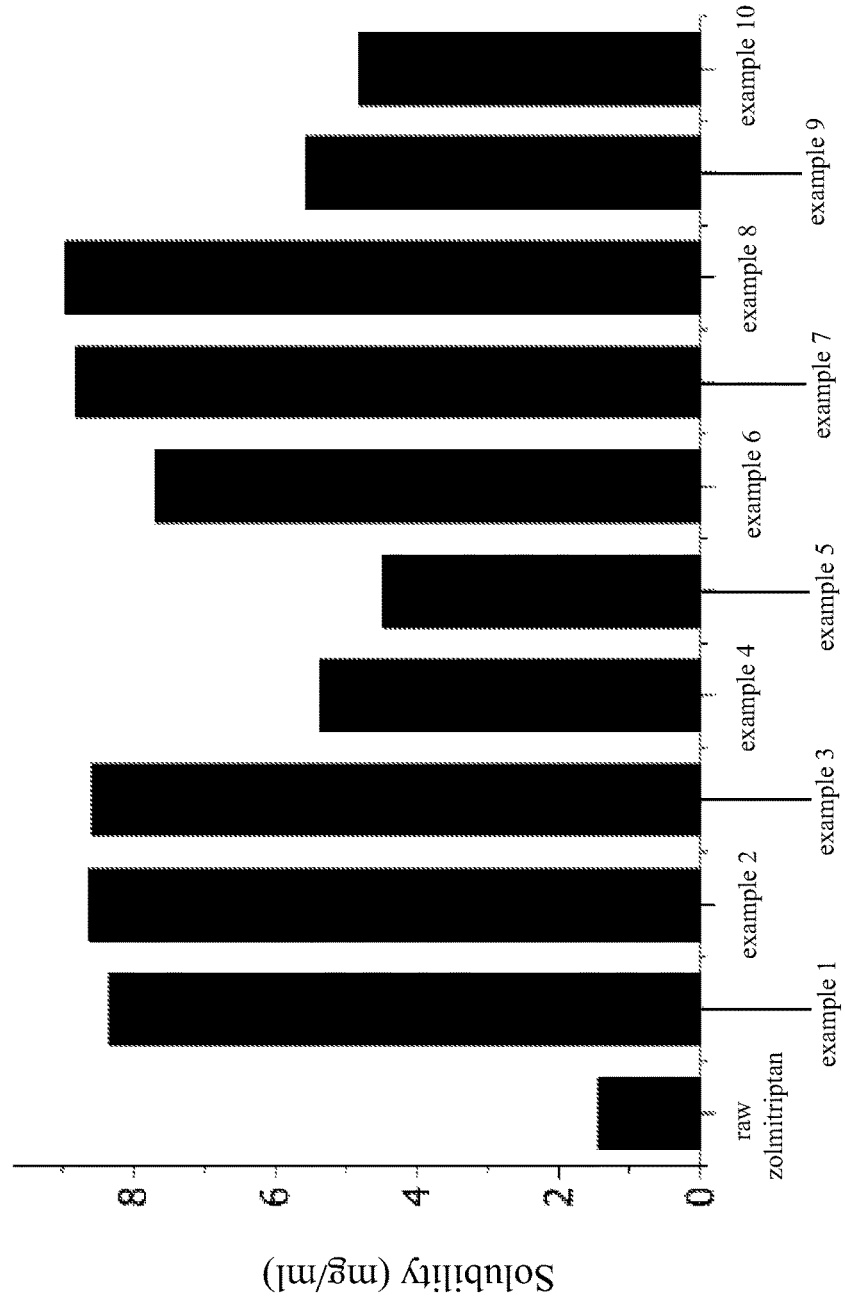
FIG. 3 illustrates the solubility test results of pharmaceutical compositions prepared in the Examples of the present invention.

As illustrated in FIG. 3, it can be confirmed that the pharmaceutical compositions in the Examples have higher solubilities than zolmitriptan, and it can be confirmed that the compositions in Examples 1 to 3 and 6 to 8 have about 4 times higher solubilities than that of zolmitriptan.

In addition, the composition of Example 5 has 2 times higher solubilities than zolmitriptan.

Thus, by mixing the saccharin in the triptan compound, it can be confirmed that the solubility is increased.

What is claimed is:

1. A pharmaceutical composition comprising an ionic liquid consisting of a triptan compound and saccharin, wherein a weight ratio of said triptan compound to said saccharin in said ionic liquid ranges from 34:66 to 82:18.

2. The pharmaceutical composition of claim 1, being liquid at a temperature ranging −30° C. to 250° C.

3. The pharmaceutical composition of claim 1, wherein said triptan compound is selected from the group consisting of zolmitriptan, sumatriptan, rizatriptan, almotriptan, naratriptan, eletriptan, avitriptan, frovatriptan, and combinations thereof.

4. A method for preparing the pharmaceutical composition of claim 1, the method comprising: preparing said ionic liquid by mixing said triptan compound and said saccharin at a weight ratio that ranges from 34:66 to 82:18, respectively.

5. The method of claim 4, wherein said ionic liquid is prepared by milling a mixture of said triptan compound and said saccharin.

6. The method of claim 4, wherein said ionic liquid is prepared by using a solvent evaporation method.

7. A method for treating migraines, sudden severe migraines, or cluster migraines in a subject, comprising administering to the subject an effective amount of the pharmaceutical composition of claim 1.

8. A method for treating migraines, sudden severe migraines, or cluster migraines in a subject, comprising administering to the subject an effective amount of the pharmaceutical composition of claim 2.

9. A method for treating migraines, sudden severe migraines, or cluster migraines in a subject, comprising administering to the subject an effective amount of the pharmaceutical composition of claim 3.

\* \* \* \* \*